(12) United States Patent
Chew

(10) Patent No.: US 11,660,298 B1
(45) Date of Patent: May 30, 2023

(54) PREVENTING THERMAL TRAUMA BY PRE-TREATMENT WITH ICILIN

(71) Applicant: Kevin Chew, Glen Rock, NJ (US)

(72) Inventor: Kevin Chew, Glen Rock, NJ (US)

( * ) Notice: Subject to any disclaimer, the term of this patent is extended or adjusted under 35 U.S.C. 154(b) by 192 days.

(21) Appl. No.: 16/945,845

(22) Filed: Aug. 1, 2020

Related U.S. Application Data

(60) Provisional application No. 62/881,985, filed on Aug. 2, 2019.

(51) Int. Cl.
| | | |
|---|---|---|
| *A61K 31/513* | (2006.01) | |
| *A61K 9/08* | (2006.01) | |
| *A61P 17/02* | (2006.01) | |
| *A61K 9/00* | (2006.01) | |

(52) U.S. Cl.
CPC .......... *A61K 31/513* (2013.01); *A61K 9/0014* (2013.01); *A61K 9/08* (2013.01); *A61P 17/02* (2018.01)

(58) Field of Classification Search
CPC .................................................. A61K 31/513
See application file for complete search history.

(56) References Cited

U.S. PATENT DOCUMENTS 8,927,605 B2 * 1/2015 Subkowski .......... C07D 401/04
514/617

OTHER PUBLICATIONS

Wang, 2015 ACR/ARHP Annual Meeting.*
Pielesz, Spectrochimica Acta Part A: Molecular and Biomolecular Spectroscopy 196 (2018) 344-352.*
Patel Journal of Pharmacology and Experimental Therapeutics (2014), 349(1), 47-55, 9.*
Hagenacker Brain Research (2014), 1557, 171-179.*
Stephen B. Hulley, Designing Clinical Research, 4th Edition, pp. 1-367, 2013.*
Liu, vol. 154, Issue 10, Oct. 2013, pp. 2169-2177.*

* cited by examiner

*Primary Examiner* — Nizal S Chandrakumar
(74) *Attorney, Agent, or Firm* — Law Office of Bridgette Y. Ahn; Thomas F. Woo

(57) ABSTRACT

The present invention comprises a method of use of Icilin as a pre-treatment to mitigate the negative effects of extreme thermal trauma to skin tissue on a cellular level. Pre-treatment with Icilin prior to exposure to a thermal trauma event is shown to improve cellular viability, reduce pro-inflammatory cytokine levels, and reduce Reactive Oxygen Species (ROS) levels. The treatment is designed to be administered in small doses at concentrations of 0.0002-0.02 nM dissolved in an aprotic polar solvent such as dimethyl sulfoxide.

4 Claims, 10 Drawing Sheets

FIG 1a
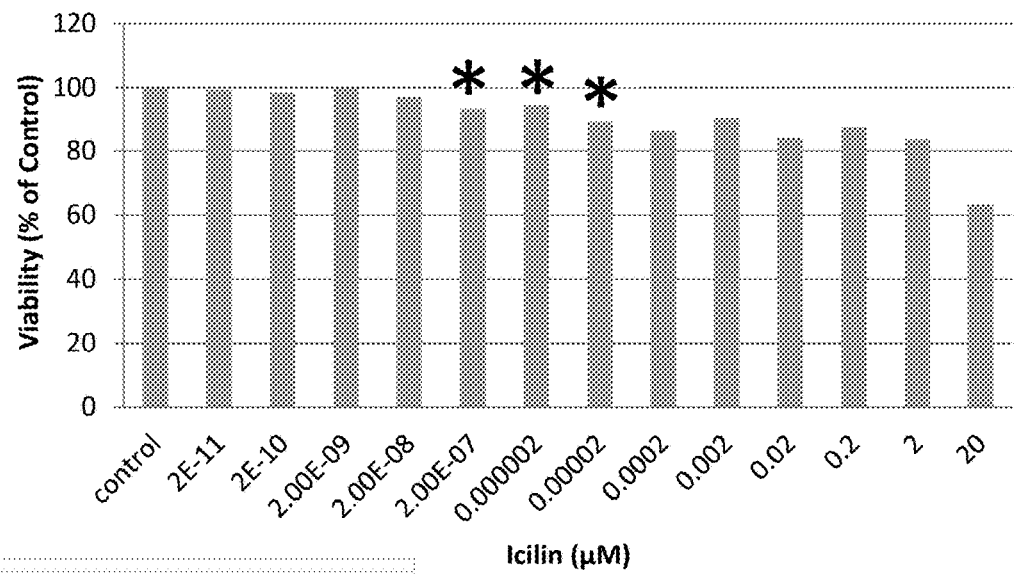
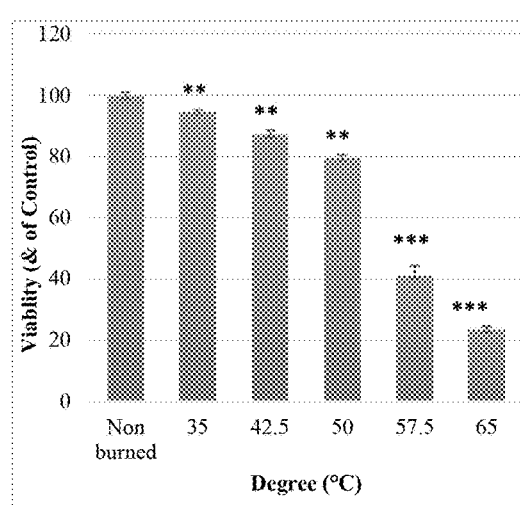
FIG. 1b
Calorimetry:
$$Third\ Degree\ Burns \approx 550 KJ\ Q$$
$$= mc\Delta T\ Mass\ of\ Plate$$
$$= 0.06195\ kg$$
$$Specific\ heat\ of\ Polystyrene$$
$$\approx 1500\ J/g\ °C\ \Delta T = 13°C\ Q$$
$$= 0.06195 * 1500 * 13$$
$$= 1.208 KJ\ Sustained\ Energy\ Transfer$$
$$= \frac{550\ KJ}{1.208\ KJ} = 455.28859 \approx 7.5\ minutes$$
FIG. 1c

PREVENTING THERMAL TRAUMA BY PRE-TREATMENT WITH ICILIN

CROSS REFERENCE TO RELATED APPLICATIONS

This application claims priority from U.S. Provisional application No. 62/881,985 filed on Aug. 2, 2019.

FIELD OF INVENTION

The present invention relates to the usage of the super-cooling chemical Ag-35 (Icilin) as a pre-treatment for subsequent serious thermal trauma afflicted to fibroblasts. By design, Icilin dissolved in an aprotic polar solvent (e.g. dimethyl sulfoxide (DMSO)) is utilized as a pre-treatment of skin to significantly promote the health of skin tissue at a cellular level when exposed to serious thermal trauma.

BACKGROUND OF THE INVENTION

Serious thermal trauma (>47° C.) to skin, particularly trauma deep enough to penetrate to the fibroblasts (3rd layer of the epidermis), results in systematic over-production of pro-inflammatory cytokines and a significant disruption to the viability of the surrounding cells. The thermally challenged region, often referred to as the central zone of necrosis, is surrounded by a potentially ischemic zone, that depending on the concurrent cellular responses (e.g. cytokine quantity, oxidative stress, or calcium levels), may mature into a delayed necrosis zone within 24-48 hours. As such, current treatments for severe thermal trauma primarily address repairing the underlying surrounding tissue, rather than the region of direct contact, and preventing the zone conversion. However, these treatments have not been able to eliminate residual scarring, disfigurement, or the resulting body-wide imbalance of the immune system.

The lack of a fully functional immune system, which is often cited as the most prevalent shortcoming of current burn recover models, often leads to sepsis, the leading cause of post-thermal trauma death. A method to simulate a cooling environment may lead to a minimization of the immune system reaction.

Studies have shown that both deceased and live thermally challenged skin cells produce extreme amounts of pro-inflammatory cytokines such as Interleukin-6 (IL-6), Interleukin-1β (IL-1β), Interleukin-8 (IL-8), and Tumor Necrosis Factor-α (TNF-α).

Excess inflammatory cytokines released by the burned cells further exacerbate cellular death due to the concurrent increase in oxidative stress. However, in an appropriate balance, pro-inflammatory cytokines are necessary for recovery. Cytokines, both inflammatory and anti-inflammatory, are used by the body as a signaling mechanism for the body's immune system to mitigate the potential damage of any environmental stimulus. In excess, as in the case following a serious burn, their overabundance can initiate a cytokine cascade and disrupt normal cytokine production in a continuous feedback loop. T-Cells are signaled to aid in the healing process and then they secrete additional cytokines, which then recruit additional T-Cells. This cycle repeatedly continues, and the immune system is overwhelmed by the significant imbalance.

For other analogous types of inflammatory responses, it has been reported that cold temperatures can reduce and even prevent the above described immune system responses from occurring. For example, a current trend in athletic recuperation is cryotherapy, where athletes will immerse themselves in a −110° C. chamber following rigorous exercise. Many top professional athletes, including Lebron James, Kobe Bryant, and Floyd Mayweather Jr., have been reported to routinely undergoing cryotherapy sessions to facilitate their physical recovery and to staunch muscular inflammatory stress. When looking at the exact cellular mechanisms behind the positive effects of cold temperatures, it appears there is significant merit to their medical application.

The sensation of the thermal injury and cold temperatures is the result of Transient receptor potential channels. Specifically, the transient receptor potential cation channel subfamily M member 8 (TRPM8) is the main ion channel responsible for the perception for feeling cold in all cells and is especially prevalent in skin cells such as fibroblasts. Upon activation by cold temperatures <21° C., extracellular calcium ions ($Ca2+$) and sodium ions ($Na+$) flood into the cytoplasm through TRPM8 channels. This increase in concentration of $Ca2+$ and $Na+$ induces the actual "sensation" of cold. TRPM8 activation also initiates a positive feedback loop that upregulates its own expression. The degree of upregulation is dependent on the activation temperature. Importantly, TRPM8 upregulation has been previously shown to interfere with and suppress pro-inflammatory cytokine TNF-α expression by way of Nuclear Factor kappa-light-chain-enhancer of activated B cells (NFκB) mediation. This agrees with previous studies have shown that activation of TRPM8 in rats may attenuate pro-inflammatory responses. Therefore, TRPM8 activation prior to a thermal injury or burns may help mitigate the enhanced release of cytokines with a potentially deleterious cytokine cascade. If the excess cytokine production can be reduced by inhibiting or preventing the cytokine cascade, may offer the potential to inhibit expansion of the delayed necrotic zone caused by a thermal injury or burn.

Super-cooling chemicals may be a potential method to provide this TRPM8 activation. Super-cooling chemicals are substances that will elicit a feeling of "cold" but with no actual temperature change They activate the same ion channels as cold temperatures and elicit the same molecular chain of events. Icilin, a super-cooling agent, is a "super-agonist" of TRPM8. A mechanism is proposed that would utilize Icilin to reduce the inflammatory response of a severe burn by mimicking cold temperatures and eliciting the same anti-inflammatory effects. Icilin may be able to restrict the over-release of cytokines IL-6, IL-1β, and TNF-α. The Icilin induced regulation of all these factors may significantly assist in the healing process for burn wounds. In addition, Icilin is an affordable and commercially available compound.

RATIONAL FOR INVENTION

Despite the frequency of burns, ranging from minor to major, there still exists a need to further improve modern burn wound recovery. This is especially true for severe thermal injuries (third-degree burns), where the initial burn damage and potential complications are multifaceted and go beyond the initial contact. The majority of burn wound treatments today are focused on the restoration of damaged tissue and preventing disfigurement and are effective in those regards. However, despite their successful elements, modern burn wound treatments fail to account for the mass inflammation that accompanies serious thermal injuries. The challenge with preventing inflammation is that it rarely constitutes the immediate fatality behind a serious burn.

Rather, the inflammation is responsible for complications that arise only after a victim survives the initial infliction of the burn. Therefore, the proposed method described is a new treatment option designed to take advantage of the supercooling chemical Icilin to combat the inflammation associated with serious burns.

SUMMARY OF INVENTION

The present invention concerns a method of pre-treatment of thermally challenged fibroblasts using Icilin at a concentration range of about 0.0002 nM to about 0.02 nM dissolved in an aprotic polar solvent, such as dimethyl sulfoxide (DMSO). The pre-treatment works effectively as an anti-inflammatory agent and viability booster if applied two to eight hours before significant thermal trauma. Fibroblasts were plated and burned in a 96 Well Plate on a microplate incubator at 50° C. for seven and half minutes. A significantly decreased cytokine presence and increased viability was consistently found.

BRIEF DESCRIPTION OF THE FIGURES

These figures and graphs are listed to illustrate the effectiveness of the model/method and provide additional evidence for the accurate lab work and techniques utilized. Bars are means±STDEV (n=5). One asterisk (*) represents p-values <0.05, two asterisks () represent p-values <0.01, and three asterisks represent (*) p-values <0.001.

FIG. 1. The figure depicts the data and calculations performed in order to create an in vitro burn model analogous to a $3^{rd}$ degree burn. FIG. 1a shows the effect on fibroblast viability of Icilin concentrations on regular non-burned fibroblasts. FIG. 1b shows a temperature effect on control fibroblast viability and FIG. 1c shows the calculation of calorimetry for the plate. In summary, the figure shows Icilin's potential cytotoxicity in fibroblasts, the effect of temperature on fibroblast viability, and calorimetry needed to create the in vitro burn model. Asterisks represent statistically significant concentrations of Iclin.

FIG. 4. The figure shows in bar charts for Icilin's the effect on pro-inflammatory cytokine Interleukin-6 (IL-6) expression.

FIG. 5. The figure shows in bar charts the effect of Icilin on pro-inflammatory Interleukin-8 (IL-8) expression.

FIG. 6. The figure shows the effect of Icilin on pro-inflammatory Interleukin-1β (IL-1β) expression.

DETAILED DESCRIPTION OF THE INVENTION

This invention revolves around the usage of Icilin as a pre-treatment to burned (thermal injury) fibroblasts. This treatment results in an increase in viability, stabilization of critical pro-inflammatory cytokines, and restoration of Reactive Oxygen Species (ROS, free radical) levels. Pro-inflammatory cytokines and free radicals, such as ROS, are both factors that lead to decreased fibroblast viability and proliferation. The restoration of their levels is what subsequently leads to the positive effects of Icilin on viability.

Figure 9:
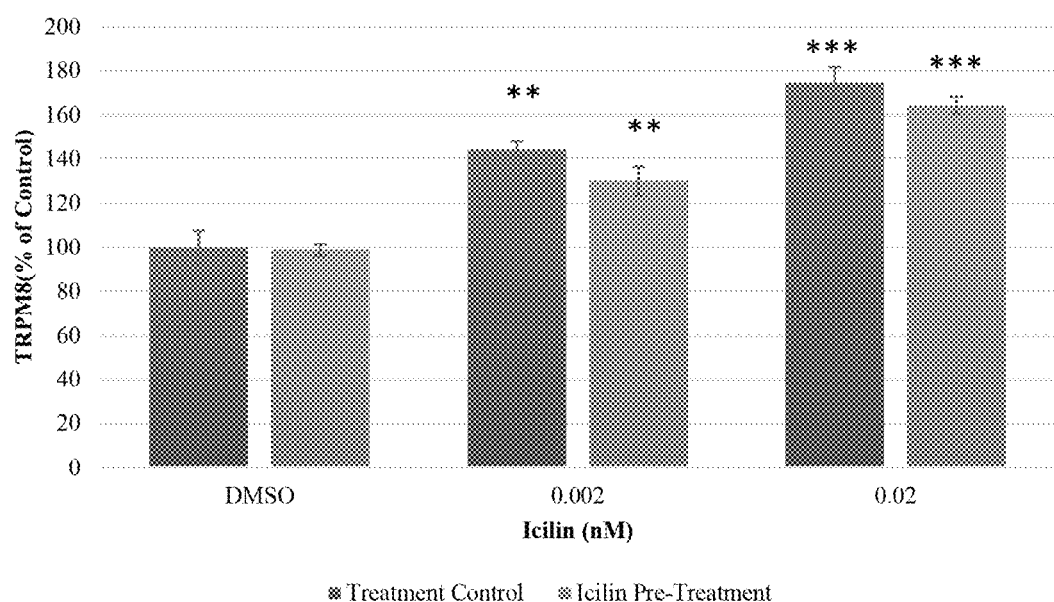
FIG. 9. The figure shows the effect of Icilin on the burned (Icilin pre-treatment prior to thermal injury, right bars) and healthy fibroblast's (controls treated with Icilin without thermal injury, left bars) levels of Transient receptor potential cation channel subfamily M member 8 (TRPM8). As expected TRPM8 expression was significantly increased for all concentrations of Icilin. This increase in TRPM8 expression was maintained for both the non-thermally challenged fibroblasts as well as the thermally challenged fibroblasts. Demonstrating that TRPM8 upregulation was maintained for the both non-thermally challenged and thermally challenged fibroblasts that Icilin's mechanism of action involves TRPM8's upregulation to block NFκB nuclear localization.

The proposed mechanism behind why Icilin produces such positive results on thermally challenged fibroblasts relates to the ion channel that Icilin works on, namely, the Transient receptor potential cation channel subfamily M member 8 (TRPM8). When confronted with cold temperatures, fibroblasts begin to upregulate the production of TRPM8 as shown in FIG. 9; the colder the temperature, the greater the upregulation. Icilin is a super-cooling chemical that is 200 times more potent than menthol (a common super-cooling chemical found in items such as mints) and is a superagonist of TRPM8. Icilin affects the channel nearly analogously to actual frigid temperatures.

NFκB mediation is proposed as the mechanism behind why Icilin is able to prevent the expression of TNF-α and subsequently other pro-inflammatory cytokines that rely on TNF-α's expression for their own transcription.

Figure 10:
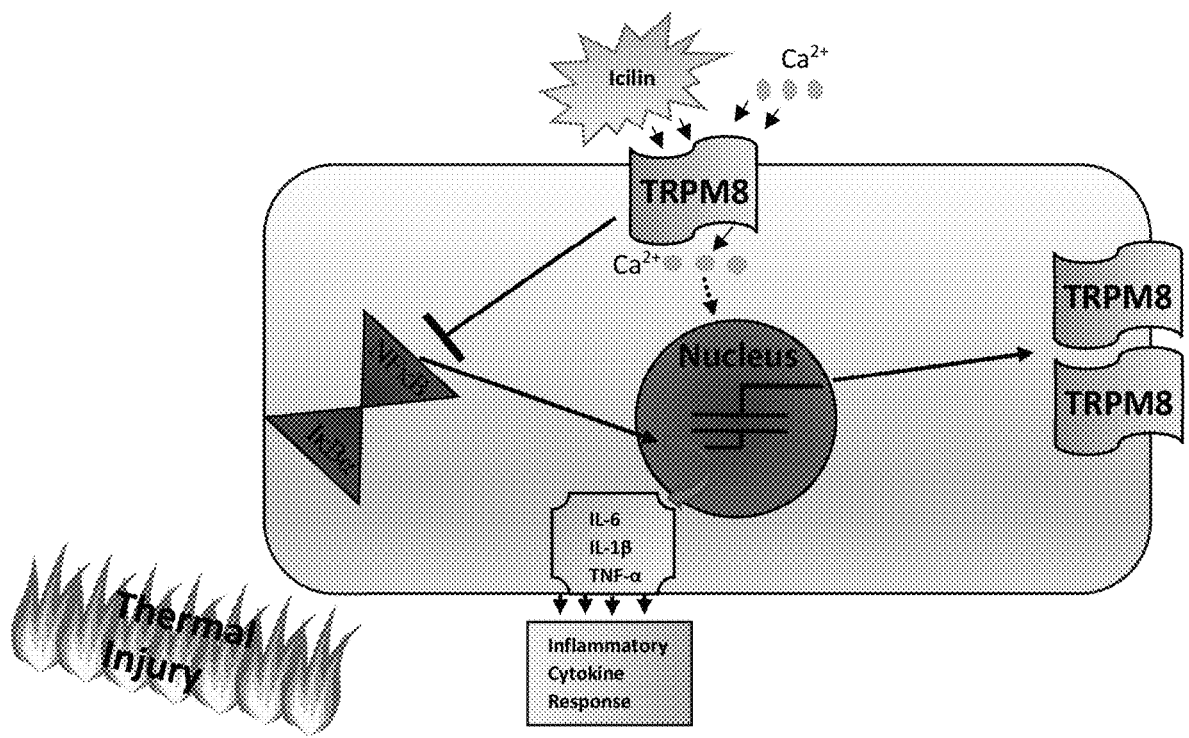
FIG. 10. The figure displays a proposed mechanism that Icilin initiates to increase the viability of burned cells and restore pro-inflammatory levels. Icilin's activation of TRPM8 induces its upregulation, blocking the upregulation of pro-inflammatory cytokines IL-6, IL-1p, and TNF-α. During thermal trauma NFκB is localized in the nucleus. However, TRPM8 transcription factors and NFκB are localized in the same sector of the nucleus, therefore allowing Icilin's upregulation of TRPM8 to halt the downstream production of cytokines.

Normally, NFκB exists in the cytoplasm as a connected species to IκBα (nuclear factor of kappa light polypeptide gene enhancer in B-cells inhibitor, alpha, see FIG. 10), its regulator. During any appropriate environmental stimulus, phosphorylation occurs in the cytoplasm resulting in NFκBp6, a substrate of NFκB, to move into the nucleus and initiate gene transcription of several inflammatory cytokines, including TNF-α, although the exact cytokines are dependent on the concurring environmental stimulus. However, it has been previously shown that both TPRM8 and NFκB transcription factors undergo nuclear localization "together" (the transcription factors can bilaterally interfere with each other) and it is this interaction that can be exploited to specifically prevent NFκB nuclearization.

Icilin has an identical effect on TRPM8 upregulation in fibroblasts as cold temperatures. As a pre-treatment, Icilin will bind to and promote the expression of TRPM8 and cause TRPM8 promoting transcription factors to localize. Then, when an environmental stimulus, such as a serious thermal trauma (burn), requires NFκB nuclear localization, the NFκBp6 is unable to localize due to TRPM8 transcription factor interference.

In summary, this invention is a novel method that utilizes Icilin (dissolved in aprotic polar solvents and in concentrations of 0.0002-0.02 nM) as a pre-treatment and preventative measure against serious thermal trauma analogous to or more extreme than a $3^{rd}$ degree burn. The usage of Icilin as a pre-treatment is proven through its action mechanism of TRPM8 and its subsequent effects.

Unless specifically indicated otherwise, all technical and scientific terms used herein have the same meaning as commonly understood by those of ordinary skill in the art to which this invention belongs.

Throughout the description and claims of this specification, the word "comprise," (and variations of the word, such as "comprising" and "comprises,") means "including but not limited to," and is not intended to exclude, for example, other additives, components, integers, or steps.

The phrase "and/or" as used herein, should be understood to mean "either or both" of the elements so conjoined, i.e., elements that are conjunctively present in some cases and disjunctively present in other cases.

As used herein, "or" should be understood to have the same meaning as defined above for "and/or". For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of", or, when used in the claims, "consisting of", will refer to the inclusion of exactly one element of a list of elements. In general, the term "or" as used herein shall only be interpreted as indicating exclusive alternatives (i.e., "one or the other but not both") when preceded by terms of exclusivity, such as "either", "one of", "only one of", or "exactly one of."

EXAMPLES

Example 1

Cell Culture and Reagents

Human Foreskin Fibroblasts (HFF) (ATCC, Manassas, Va.) were cultured in Dulbecco's Modified Eagle Medium Nutrient Mixture F-12 with 10% Fetal Bovine Serum, 1% penicillin streptomycin. 0.05% Trypsin EDTA was used for subculture (Invitrogen, Grand Isl., N.Y.). Cells were incubated at 370 Celsius and 5% $CO_2$, and grown in 96 well, T25 or T75 Corning Tissue Culture vessels. When cells became confluent, they were trypsinized using 0.05% trypsin/EDTA. Cells used for the various assays were plated at $0.2 \times 10^6$ cells/mL unless otherwise noted. Fibroblasts were selected due to their critical role in skin wound recovery. Fibroblasts were fluorescently imaged with a Nikon Eclipse TS100 Microscope (Nikon, Melville, N.Y.).

Example 2

In Vitro Burn Model and Icilin Treatment

An in vitro burn model was created to replicate the severity of a third-degree burn. Cells were plated in a Polystyrene 96 Well Plate (100 μL per well) then burned in a VWR Incubating Micro Plate Shaker (VWR, Bridgeport, N.J.) via its adjustable heat setting. Thermal trauma (burning) was determined to take place at 50° C. for a total of 7.5 minutes (FIG. 1b). This temperature represented cell viability >50% 24 hours after the thermal injury treatment. Temperature of plate was confirmed using a Fluke 63 Infrared Thermometer (Fluke, Phoenix, Ariz.).

Icilin (Cayman Chemicals, Ann Arbor, Mich.) was tested both as a pre-treatment (eight hours prior to being thermally injured) and post-treatment (eight hours after receiving thermal injury) to the thermally challenged fibroblast cells.

A concentration range of 0.0002-0.02 nM dissolved in aprotic polar solvent DMSO (Sigma-Aldrich, St. Louis, Mo.) was used.

Example 3

MTS and Trypan Blue Exclusion Assays to Measure Proliferation and Viability

Proliferation was determined using the MTS assay. Approximately 24 hours after burning, 15 µL of Cell Titer 96 Aqueous One Solution Reagent (Promega, Madison, Wis.) was added to each well of a 96-well plate containing 100 µL of complete growth media. The 96-well plate was incubated at 37° C. for 1 hour. The 96-well plate was read to measure absorbance at 490 nm using a microplate reader (BioTek, Winooski, Vt.). Viability was determined by trypan blue exclusion assays. Approximately 24 hours after burning, 500 µL of trypsinized cells were loaded into the Vi-CELL×4 Cell Viability Analyzer (Beckman Coulter, Indianapolis, Ind.) for analysis.

Example 4

Lysate Preparation Indirect ELISA

Approximately 24 hours after burning, cells were trypsinized and centrifuged at 1200 rpm for 7 minutes. Cells were then washed in phosphate-buffered saline (Thermo Fisher Scientific, Fair Lawn, N.J.) and re-suspended in 1 mL of 1×lysis buffer #9803 (Cell Signaling Technology, Danvers, Mass.) containing protease cocktail inhibitor #P8340 (Sigma-Aldrich, St. Louis, Mo.) at 1×106 cells per 1 mL of solution. Afterwards, cells were incubated on ice for 10 minutes and centrifuged at 13000 rpm for 15 minutes at 4° C. Lysates were collected and stored at −80° C.

Example 5

General Indirect Antibody Enzyme-Linked Immunosorbent Assay (ELISA) Protocol

Figure 2:
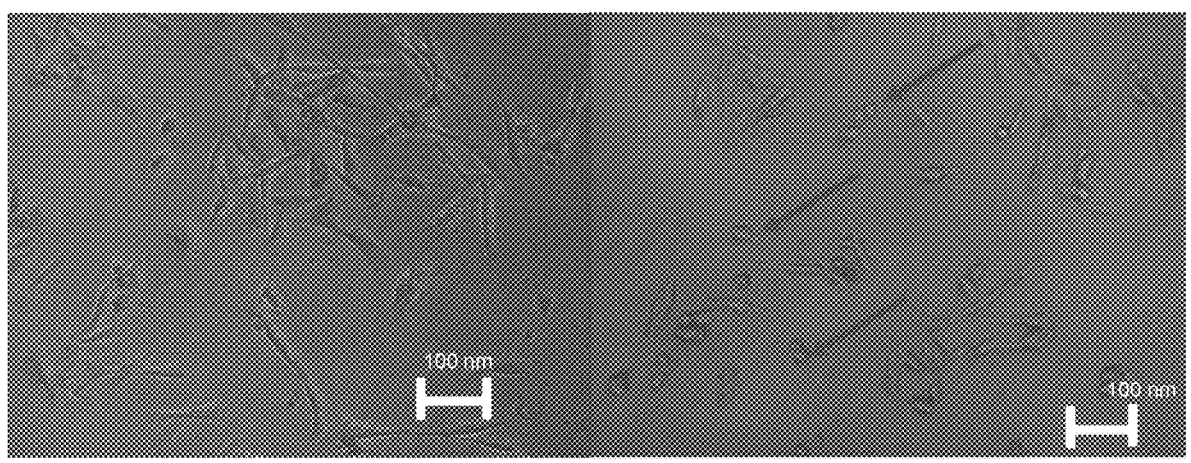
FIG. 2. The left frame displays an image of normal healthy fibroblasts and the right frame shows an image of burned fibroblasts showing the effectiveness of the in vitro burn model. Arrows signify fibroblast detachment.
Figure 3:
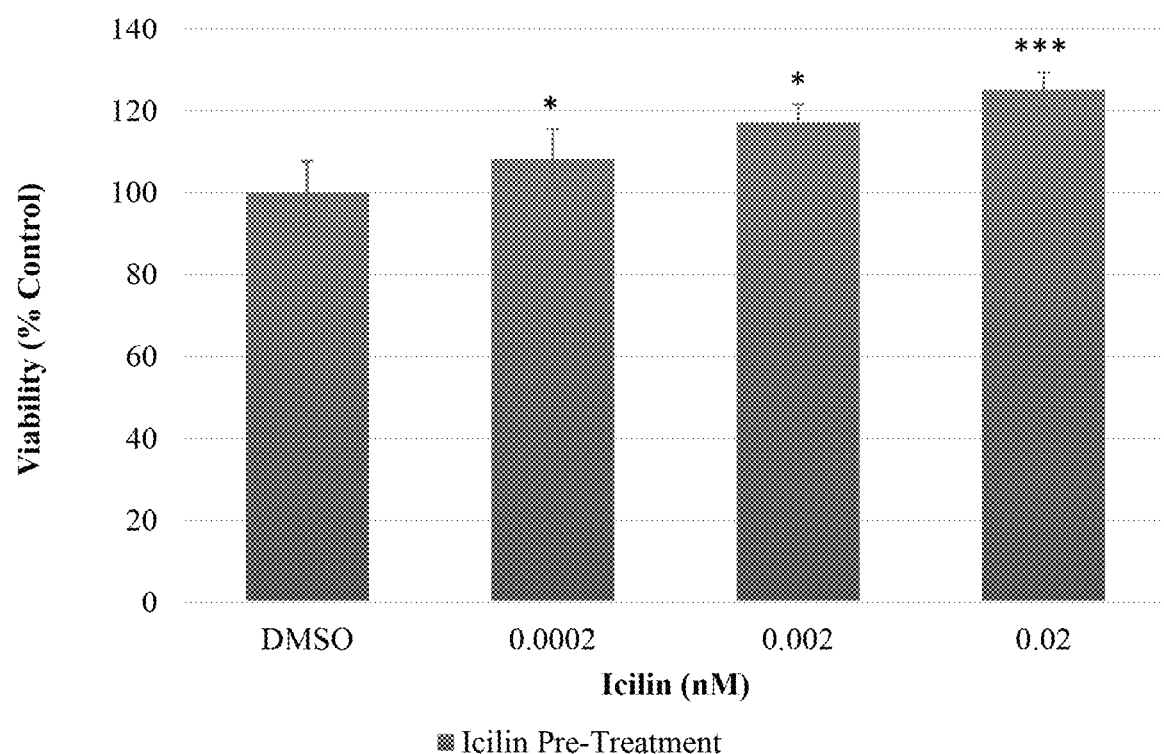
FIG. 3. The figure shows the effect of pre-treatment with Icilin concentrations on fibroblast viability data in the in vitro burn model. The fibroblast viability increases with increasing concentrations of Icilin. While the viability of the pre-treated burned fibroblasts did not match those of healthy fibroblasts, it was still significantly higher than the untreated burned fibroblasts for all tested concentrations.
Figure 4A:
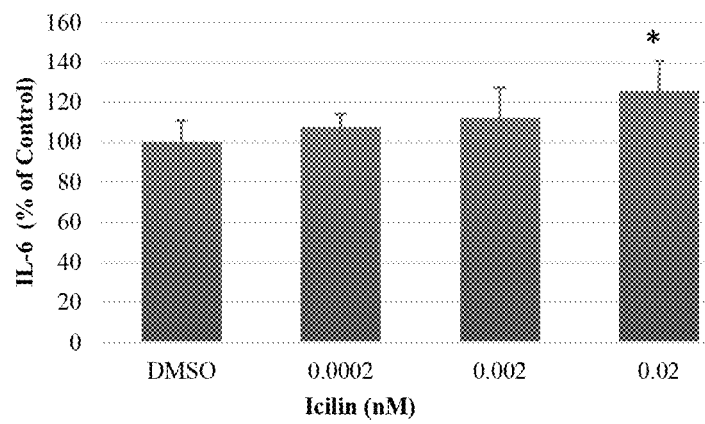
In FIG. 4a the effect of Icilin on non-thermally challenged fibroblasts, Icilin increased IL-6 expression as any external stimulus would.
Figure 4B:
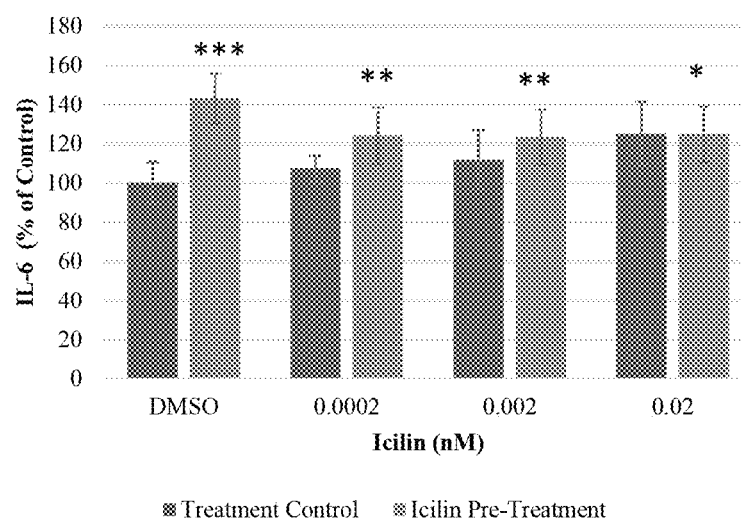
FIG. 4b left bars are the corresponding bars shown in FIG. 4a for non-thermally challenged fibroblasts while the right bar show the effect of Icilin concentration pre-treatment on the thermally challenged fibroblasts. In thermally challenged fibroblasts, Icilin produces a significant decrease in IL-6 expression. The greater the concentration of Icilin, the larger the decrease in IL-6. This corresponds to the results found in FIG. 3 where the Icilin pre-treatment significantly increased the viability, with the higher concentrations of Icilin providing the greatest viability increase. The data suggests the decrease in IL-6 relates to the increase in viability.
Figure 5A:
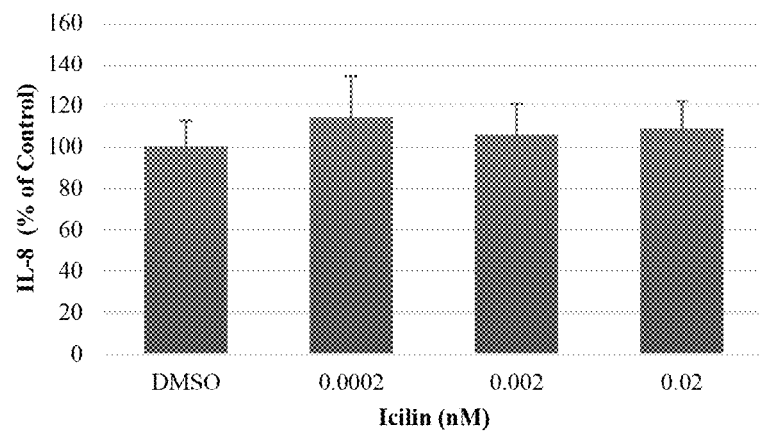
In FIG. 5a, the effect of increasing concentrations of Icilin in fibroblasts that were not exposed to thermal treatment.
Figure 5B:
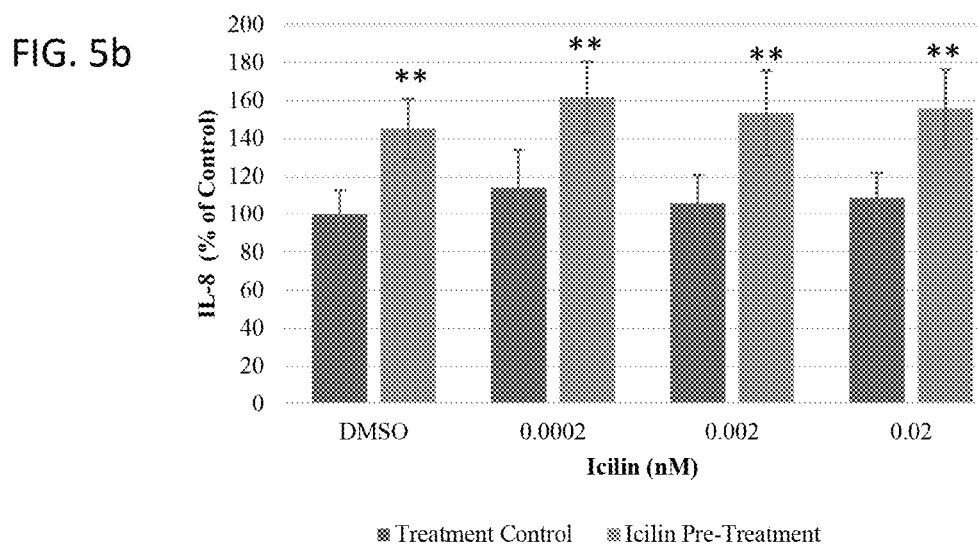
FIG. 5b left bars are the corresponding bars from FIG. 5a non-thermally challenged fibroblasts while the right bars show the effect Icilin concentrations pre-treatment on the thermally challenged fibroblasts. The only factor that appeared to have any impact on IL-8 expression was the infliction of a thermal injury. This suggests that Icilin has no noteworthy effect on IL-8 expression and that Icilin's effect on viability has no bearing on IL-8 expression.
Figure 6A:
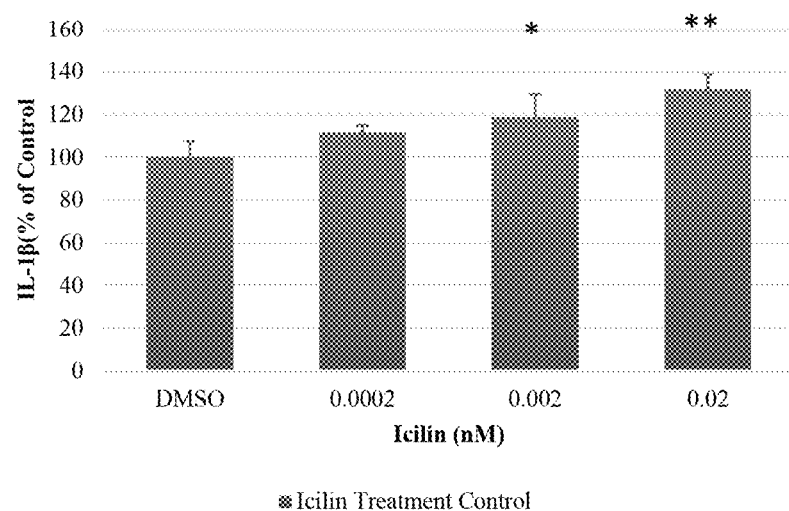
In FIG. 6a, the effect of increasing concentrations of Icilin in fibroblasts that were not exposed to thermal treatment. As the concentrations of Icilin increase IL-1β expression also increases. A similar effect to that observed for IL-6 expression (see FIG. 4a).
Figure 6B:
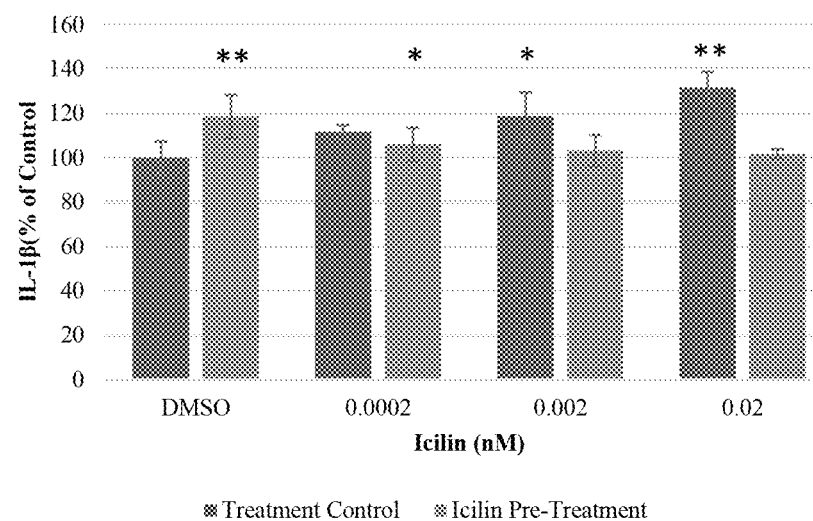
In FIG. 6b, left bars of the bar are the corresponding bars from FIG. 6a non-thermally challenged while the right bars show the effect of Icilin concentrations pre-treatment on the thermally challenged fibroblasts. As shown in the bar chart in FIG. 6b, when Icilin was applied to the thermally challenged fibroblasts, a decreasing trend in IL-6 expression was observed with increasing concentrations of Icilin. The decrease was significant enough that the IL-1β levels at all Icilin concentrations were below the levels of the non-thermally challenged fibroblasts that received the same concentration of Icilin.
Figure 8A:
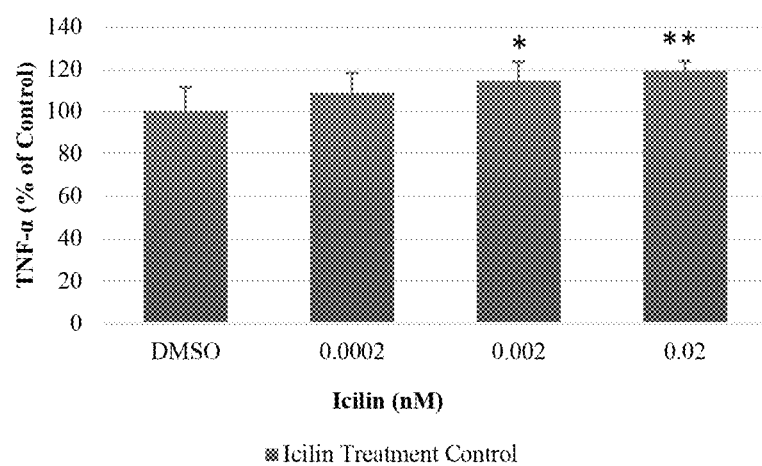
FIG. 8. The figure shows the effect of Icilin on Tumor Necrosis Factor-α (TNF-α) levels in fibroblasts pre-treated with Icilin before thermal treatment and healthy fibroblasts treated with Icilin without thermal treatment ((control). When Icilin was applied to fibroblasts, a steady increase in TNF-α expression was observed as the concentrations increased (FIG. 8a). The results show a similar trend to Icilin's effect on IL-6, which is expected, given the precursory relationship between TNF-α and IL-6. When Icilin was applied to the thermally challenged fibroblasts (FIG. 8b, right bars), it again had a similar trend to that of the IL-6 expression. As the concentrations of Icilin increased the TNF-α expression dropped significantly.
Figure 8B:
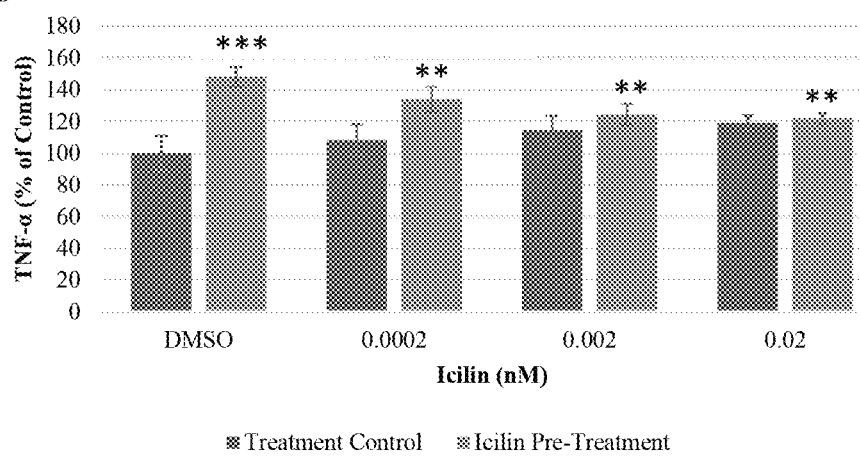

To perform indirect ELISA, 100 µL of lysates or cell medium (following the infliction of a thermal injury) was pipetted into a 96-well plate and incubated overnight at 4° C. Following incubation, the 96-well plate was emptied of all contents and 300 µL of 1×BSA Diluent/Blocking Solution (KPL, Gaithersburg, Md.) were added to each well. After ten minutes, each well was treated with a primary antibody diluted to 1:300 for Interleukin 6 (IL-6) (FIG. 4), Interleukin 8 (IL-8) (FIG. 5), Interleukin-1β (IL-1β) (FIG. 6), Tumor Necrosis Factor Alpha (TNF-α) (FIG. 8), and Heat Shock Protein 90 (HSP90) protein (Abcam, Cambridge, Mass.) and incubated at room temperature. After 1 hour, the 96-well plate was washed 5 times with 1×wash solution (KPL, Gaithersburg, Md.). Then, each well was treated with a horseradish peroxidase-labeled goat anti-rabbit polyclonal secondary antibody (Life Technologies, Carlsbad, Calif.) diluted to 1:500 and incubated at room temperature. After 1 hour, the 96-well plate was washed 5 times with 1×wash solution (KPL, Gaithersburg, Md.). Then, each well was treated with 100 µL of ATBS substrate solution (KPL, Gaithersburg, Md.). The 96-well plate was read to measure absorbance at 405 nm in a microplate reader (BioTek, Winooski, Vt.).

Example 6

Measurement of Reactive Oxygen Species (ROS)

Figure 7:
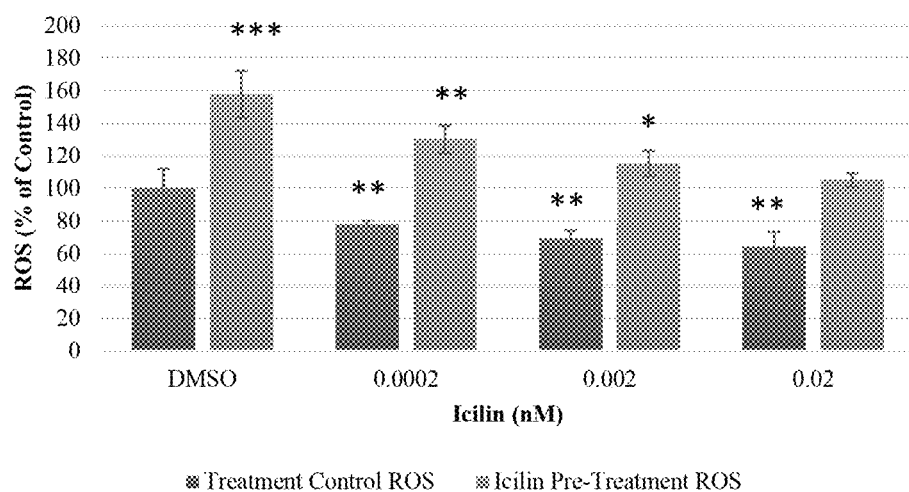
FIG. 7. The figure shows the effect of increasing concentrations of Icilin in burned (pre-treatment, right bars) and healthy fibroblast's (left bar, control) on Reactive Oxygen Species (ROS) levels. Icilin significantly reduces ROS levels in non-thermally challenged fibroblasts at all concentrations. Additionally, Icilin's ability to reduce ROS levels was observed in the thermally challenged fibroblasts. This suggests that Icilin at 0.02 nM will essentially restore ROS levels of thermally challenged fibroblasts to their normal quantities.

ROS was measured through ROS-Glo™ H2O2 Assay (Promega, Madison, Wis.). Fibroblasts were plated in 96-Well plates and thermal injury was inflicted. ROS-Glo™ Detection Solution was reconstituted (50 reaction wells) comprised of 5 mL Luciferin Detection Reagent, 50 µl d-Cysteine, and 50 µl Signal Enhancer Solution. Eighteen hours after the trauma, 20 µl of $H_2O_2$ Substrate solution comprised of 1.0 mL $H_2O_2$ Substrate Dilution Buffer (Promega, Madison, Wis.) and 12.5 µl $H_2O_2$ Substrate (Promega, Madison, Wis.) was added to each reaction well. After six hours, 100 µl ROS-Glo™ Detection Solution was added to each well. The well plate was then incubated at room temperature for 20 minutes then measured for luminescence (see FIG. 7).

Example 7

Statistical Analyses

Statistical and computational biology analyses were performed using Microsoft Excel. Student's t-test (unpaired, two-tailed) was performed in Excel with n≥5 and α=0.05. On the graphs, bars represent mean+/−standard deviation. Data was corrected to "per cell" and then to "% control per cell." One asterisk (*) represents p-values <0.05, two asterisks () represent p-values <0.01, and three asterisks represent (*) p-values <0.001. All assays were repeated at least three times.

I claim:

1. A method of preventing thermal trauma and/or injury to a tissue area in a subject comprising application of Icilin dissolved in dimethyl sulfoxide to the tissue area prior to exposure to the thermal trauma and/or injury, wherein the Icilin is dissolved in dimethyl sulfoxide at concentrations ranging from 0.0002 nM to 0.02 nM, wherein the application of Icilin in dimethyl sulfoxide to the tissue area occurs 2 to 8 hours prior to exposure to thermal trauma and/or injury.

2. The method of claim 1 wherein the tissue area is an area of skin and/or dermis tissue.

3. The method of claim 2 wherein the application of Icilin is to the area of skin and/or dermis tissue results in cellular contact with skin or dermis fibroblast cells.

4. The method of claim 1 wherein the thermal trauma and/or injury is a third-degree burn.

* * * * *